US005827696A

United States Patent [19]
Estes

[11] Patent Number: 5,827,696
[45] Date of Patent: Oct. 27, 1998

[54] SYNTHESIS AND IMMUNOGENICITY OF ROTAVIRUS GENES USING A BACULOVIRUS EXPRESSION SYSTEM

[75] Inventor: Mary K. Estes, Friendswood, Tex.

[73] Assignee: Baylor College of Medicine, Houston, Tex.

[21] Appl. No.: 475,907

[22] Filed: Jun. 7, 1995

Related U.S. Application Data

[62] Division of Ser. No. 385,993, Feb. 9, 1995, which is a continuation of Ser. No. 922,582, Jul. 29, 1992, abandoned, which is a division of Ser. No. 947,773, Dec. 30, 1986, Pat. No. 5,186,933.

[51] Int. Cl.$^6$ ............................ C12N 15/46; C12N 15/64
[52] U.S. Cl. .................................... 435/91.41; 435/172.3; 435/320.1; 435/235.1; 536/23.72
[58] Field of Search .............................. 435/172.3, 320.1, 435/235.1, 69.1, 69.3, 91.41; 536/24.72

[56] References Cited

U.S. PATENT DOCUMENTS 4,853,333 8/1989 Hsaio et al. ......................... 435/172.3
4,861,845 8/1989 Atkinson et al. ....................... 530/324

OTHER PUBLICATIONS

Summers, M.D. et al. 1985. In:*Genetically Altered Viruses and the Environment*, ed. B. Fields, 22 Banbury Report, Cold Spring Harbor Laboratory, Cold Spring Harbor, N.Y., pp. 319–331.

*Primary Examiner*—Mary E. Mosher
*Attorney, Agent, or Firm*—Fulbright & Jaworski L.L.P.

[57] ABSTRACT

A method to express rotavirus genes in a baculovirus system. Different clones are used to express rotavirus genes for all of the viral proteins. These proteins are isolated in their native conformation. Some of these proteins show antigenic properties and are used to vaccinate human, agricultural animals and pet animals against diarrheal disease. The antigenic proteins are also used to detect the presence of the viral infectious agent either by themselves or in conjunction with antibodies produced against the antigenic proteins.

3 Claims, 8 Drawing Sheets

SYNTHESIS AND IMMUNOGENICITY OF ROTAVIRUS GENES USING A BACULOVIRUS EXPRESSION SYSTEM

This is a division of application Ser. No. 08/385,993, filed Feb. 9, 1995, which is a continuation of application Ser. No. 07/922,582, filed Jul. 7, 1992, abandoned, which is a division of application Ser. No. 06/947,773, filed Dec. 30, 1986, U.S. Pat. No. 5,186,933.

This invention was supported in part through grant number NIH AM30144 from the National Institutes of Health. The U.S. government may have certain rights to this invention.

FIELD OF THE INVENTION

The present invention relates generally to a method for expression of rotavirus genes in a baculovirus system. More specifically, the invention relates to the expression of rotavirus genes using a baculovirus vector for the production of antigens to be used in the detection of gastrointestinal disease caused by rotaviruses and in the development of vaccines against rotavirus infections.

BACKGROUND OF THE INVENTION

The recognition that rotavirus is an important etiologic agent of life-threatening infantile diarrheal disease has led to significant efforts to control the virus and to prevent the disease. Estes et al., "Rotavirus Antigens". In Atassi and Backrach eds., Immunobiology of proteins and peptides-III. Plenam New York p. 201–14 (1985); and Kapikian, A. Z., et al. In Fields, B. N., et al. (eds.), Virology, Raven Press, New York, p. 863–906 (1985). Although it is known that oral rehydration is an effective method for reducing diarrheal disease mortality, other interventions are needed to reduce morbidity and possibly eradicate this disease. Eradication of the disease would require immunization on a global population basis. This immunization could involve the live attenuated pathogens themselves or pathogen-specific antigenic proteins that induce neutralizing protection from disease (possibly mediated by antibodies). Elucidation and understanding of the rotavirus gene structure will greatly facilitate the efforts to eradicate the disease.

There are several problems associated with efficacy and safety when using live rotavirus vaccines:

(1) A vaccine that only produces a "mild" form of the disease may not provide safe and effective immunization in the gastrointestinal tract. Although viruses are relatively efficient in inducing resistance to subsequent infection, resistance induced by oral vaccination with attenuated virus strains may show more variability.

(2) There are significant risks that the attenuated virus will revert to virulence.

(3) Although the live vaccines may be efficious and safe when tested or used in children from developed countries, there is no guarantee that the same vaccine will be safe in children in developing countries. This is a serious concern since the susceptibility to diarrheal disease is enhanced in children in developing countries due to malnutrition and/or concurrent infections from other pathogens.

(4) Because of the expense of production and safety testing, the cost of distributing live vaccines in developing countries, where they are needed the most, may be prohibitive.

(5) Finally, in developing countries concurrent infections with multiple enteric pathogens may interfere with vaccine "takes".

The genome of rotavirus consists of 11 segments of double-stranded RNA. The genomic RNA is enclosed within a double-layered protein capsid that consists of the structural proteins VP1 to VP9. Estes, M. K. et al, "Rotavirus Antigens". In Atassi and Bachrach eds., Immunobiology of proteins and peptides-III. Plenum, New York p. 201–14 (1985). Each genome segment encodes at least one protein. Chan, W. K., et al., Virology 151:243–252, (1986), and Mason, B. B., et al., J. Virol, 46:413–423, 1983. The outer capsid protein VP3 functions as a viral hemagglutinin and also plays a role in inducing neutralizing antibodies. VP7 is an outer capsid glycoprotein which also induces neutralization antigen antibodies; VP7 is reportedly the all-attachment protein. The major capsid protein, VP6, is located on the inner capsid. This protein comprises greater than 80% of the protein mass of the viral particle and contains the subgroup antigen (S antigen VP6). Estes, M. K., et al., "Rotavirus Antigens" In M. Z. Atassi et al. (eds.) Immunology of Proteins and Peptides-III, Plenum, New York, pp. 201–214 (1985). The presence of VP6 on virus particles has been associated with viral polymerase activity. Bican, P., et al., J. Virol, 6:1113–1117 (1982). VP6 interacts with viral proteins during replication and assembly. Estes, M. K., et al., "Rotavirus Antigens" In M. Z. Atassi et al. (eds.) Immunology of Proteins and Peptides-III, Plenum, New York, pp 201–214 (1985). Although this interaction is not completely understood, it involves binding to RNA genomic segments or transcripts. VP6 possesses an oligomeric, possibly trimeric, confirmation. Gorziglia, M. C. et al., J. Gen. Virol, 66:1889–1900 (1985). Additionally, VP6 is the major protein detected in diagnostic enzyme-linked immunosorbent assays. Beards, G. M., et al., J. Clin. Microbiol, 19:248–254 (1984). Neutralizing and protective antibodies are produced to the outer capsid VP7 and VP3 antigens, but information on the role of other structural proteins, VP1, 2, 6, and 9, in inducing protection from infection is less clear. Furthermore, other gene products, for example, non-structural proteins (NS 35, 34, 28) are also synthesized by the rotavirus genome.

The expression vector system is from the insect baculovirus *Autographa californica* nuclear polyhedrosis virus (AcNPV). AcNPV has a genome of ca. 130 kilobases of double-stranded, circular DNA and it is the most extensively studied baculovirus. Miller, L. K., pp. 203–274 (1981). AcNPV has a biphasic replication cycle and produces a different form of infectious virus during each phase. Between 10 and 24 h postinfection (p.i.), extracellular virus is produced by the budding of nucleocapsids through the cytoplasmic membrane. By 15 to 18 h p.i., nucleocapsids are enveloped within the nucleus and embedded in a paracrystalline protein matrix, which is formed from a single major protein called polyhedrin. In infected *Spodoptera frugiperda* (fall armyworm, Lepidoptera, Noctuidae) cells, AcNPV polyhedrin accumulates to high levels and constitutes 25% or more of the total protein mass in the cell; it may be synthesized in greater abundance than any other protein in a virus-infected eukaryotic cell.

Polyhedrin is encoded by the virus, and the gene has been mapped and sequenced. The presence or expression of the polyhedrin gene is not required for the production of infectious extracellular virus. Inactivation of the polyhedrin gene by deletion or by insertion results in mutants that do not produce occlusions in infected cells. These occlusion-negative viruses form plaques that are different from plaques produced by wild-type viruses, and this distinctive plaque morphology is useful as a means to screen for recombinant viruses.

SUMMARY OF THE INVENTION

It is therefore, an object of the present invention to produce a recombinant molecule comprising the polyhedrin gene promoter of baculovirus *Autographa californica* nuclear polyhedrosis virus and a structural gene of a rotavirus.

Another object of the present invention is to provide a vaccine against rotavirus diarrheal disease.

It is a further object of the present invention to form a recombinant molecule comprising the strong polyhedrin gene promoter and a rotavirus outer capsid protein gene.

Another object of the present invention is to form a recombinant molecule comprising the strong polyhedrin gene promoter and a rotavirus inner capsid protein gene.

Furthermore, it is an object of the present invention to form a recombinant molecule comprising the strong polyhedrin gene promoter and a rotavirus non-structural protein gene.

It is an additional object of the present invention to form a recombinant molecule comprising the strong polyhedrin gene promoter and more than one rotavirus gene.

Additionally, it is an object of the present invention to provide a simple assay for rotavirus infection in humans and animals.

Another object of the present invention is to produce antibodies to rotavirus.

A further object of the present invention is to provide sufficient protein to elucidate its structural characteristics.

An additional object of the present invention is to provide sufficient protein to elucidate its functional properties.

A further object of the present invention is a test kit to facilitate testing for rotavirus infection in developed and developing countries.

One aspect of the present invention is the provision of a recombinant molecule, comprising a baculovirus gene promoter, at least one rotavirus gene, the promoter being in spatial relation to the gene so that it regulates the expression of the rotavirus gene. Advantageously, the promoter is the baculovirus polyhedrin gene promoter and the gene is selected from the group of rotavirus genes consisting of gene 1, gene 2, gene 3, gene 4, gene 5, gene 6, gene 7, gene 8, gene 9, gene 10, gene 11, and any combination thereof. Specific embodiments have employed the simian SA11 genes 6, 9 and 10 to produce VP6, VP7 and NS28 proteins respectively. After gene expression, the proteins are isolated in their native state.

There is provided in accordance with another aspect of the present invention a method of producing the recombinant molecule comprising the steps of inserting at least one rotavirus gene into a baculovirus transfer vector, then transferring the rotavirus gene in the baculovirus transfer vector to the baculovirus *Autographa californica* nuclear polyhedrosis virus genome DNA by cotransfection of *Spodoptera frugiperda* cells with wild type *Autographa californica* nuclear polyhedrosis virus DNA, subsequently selecting the recombinant polyhedrin promoter-rotavirus gene containing the inserted rotavirus DNA molecule by identifying virus containing occlusion-negative plaques, and finally purifying the plaques to obtain recombinant molecule virus stocks. Advantageously, the gene is selected from the group of rotavirus genes consisting of gene 1, gene 2, gene 3, gene 4, gene 5, gene 6, gene 7, gene 8, gene 9, gene 10, gene 11 and any combination thereof.

Furthermore, another aspect of the present invention is that antibodies can be produced to rotavirus proteins by a method comprising the steps of synthesizing the rotavirus protein with the recombinant molecules, subsequently innoculating intramuscularly, orally or intraperitoneally a host animal with the protein to produce an antibody and isolating and purifying the antibodies thus produced.

Another aspect of the invention is the detection of rotavirus in human biological specimens with a method comprising the steps of contacting the biological specimen with antibodies so that the antibodies and rotavirus bind to form an antibody—rotavirus complex and measuring the amount of this complex to determine the amount of rotavirus in the biological specimen.

In order to facilitate the use of the antibody to measure rotavirus infection in both developed and developing countries a test kit comprising the antibody, an appropriate means for collecting and analyzing the biological sample, has been prepared. The means for collecting and analyzing in the preferred embodiment include stool collection containers, all reagents for diluting and testing the stool and the appropriate container to run the tests.

Additionally, in the present invention a vaccine to rotavirus is produced from the group of proteins consisting of VP1, VP2, VP3, VP4, VP6, VP7, VP9, NS35, NS34, NS28 and any combination thereof. These proteins are synthesized from recombinant molecules. The antigen can be a mixed antigen formed by coexpression of genes of recombinant molecules or formed by synthesizing individual proteins with subsequent mixing of the proteins in vitro.

Immunizing and/or prophylaxis of humans and animals against rotavirus gastrointestinal disease is achieved by parenterally or by orally administering an immunological effective dose of the vaccine or a dose which will delay the onset and decrease the symptoms of the rotavirus infection. Additionally, immunization may be achieved by active immunization of the vacinee (infant, adult or animal) or through passive immunization of the infant or young animal by immunization of the mother prior to birth.

The structure and function of the rotavirus proteins can be determined by producing sufficient quantities of the rotavirus protein from the recombinant molecules for structural analysis, for functional analysis and for analysis of the immune response to specific viral proteins. Analysis of structure and function will increase our understanding of the immunological, biochemical and pathological effects of rotavirus disease.

The present invention describes the cloning and expression of individual protein products. Analysis of the antigenic, functional and molecular properties of the expressed gene products allows examination of the intrinsic and functional properties of each gene product. Thus the present invention provides an increased understanding of each individual protein in the virus structure, preparation and assembly. In addition, the present invention provides for easy and direct dissection of the humoral and cell mediated immune responses to specific viral proteins because of the availability of high levels of the individual proteins. Furthermore, the large amounts of immunogenic structural proteins facilitates vaccine testing and the production of inexpensive diagnostic tests.

The present invention describes the formation of recombinant molecules each containing a rotavirus gene or genes downstream from a highly active promoter gene of the baculovirus *Autographa californica* nuclear polyhedrosis virus (AcNPV). This expression vector system provides for synthesis of the major proteins of the simian rotavirus SA11 in insect cells. This baculovirus expression system efficiently produces the SA11 proteins from recombinant molecules containing the promoter gene and the RNA genome segment. This includes the proteins of the outer capsid, the inner capsid and non-specific proteins. The major proteins which have been produced by this expression system are VP6, VP7 and NS28. One skilled in the art will readily recognize the different classes of proteins thus produced and will appreciate the applicability of the present invention for the expression of all of the rotavirus genes.

Immunological and biochemical analysis indicates that the protein produced by the baculovirus vector system possesses both the native antigenic determinants and an oligomeric confirmation. One skilled in the art will recognize that the availability of large amounts of these proteins facilitates the determination of the intrinsic biochemical and functional properties of these proteins in the rotavirus replication processes and viral morphogenesis and increases the immunogenicity of these proteins as a vaccine.

The baculovirus possesses several characteristics which make it ideally suited as an expression vector for cloned eukaryotic genes. These include:

(1) The ability of this rod-shaped virus to encapsidate its own viral DNA containing large pieces of foreign DNA inserted into the non-essential polyhedrin gene;

(2) The presence of a very strong promoter which continues to direct transcription late in infection after extracellular virus is produced and after host genes and most viral genes are turned off. Thus the proteins controlled by this promoter are often easily distinguishable from host background proteins;

(3) The invertebrate cell cultures used with this vector are not derived from insect vectors that harbor human or animal diseases, are not susceptible to human pathogens and do not contain any undesirable genes, such as, oncogenes. The use of these cultures thus simplifies the costs of biological safety testing procedures for recombinant DNA products using this vector;

(4) The host range of the present strain of the vector is limited to cultured lepidoptera cells;

(5) Since AcNPV is currently being considered for agriculture use as a viral insecticide to control certain lepidoptera and insect pests, all safety tests required by the Environmental Protection Agency have been completed and the vector has been certified for human use;

(6) The recombinant progeny viruses produce plaques that do not contain occlusions and thus the engineered recombinants can be easily identified;

(7) Recombinant virus stocks of high titer can be easily produced to infect cells for protein production.

This expression vector has been successfully used to express several foreign eukaryotic and prokaryotic genes including β-interferon (yields 1–5 mg/l) and chloramphenicol acetyl transferase (yields 50–100 mg/l). The proteins synthesized with this vector system have been shown to be correctly processed, i.e., β-interferon was glycosylated and the amino terminal signal sequences were correctly removed. The protein products, whether glycosylated or not, have sometimes been secreted from the infected cells into the media. Since the media components can be controlled, the purification of the desired gene product from the media can be simplified. Large-scale production by fermentation processes is possible because the invertebrate insect cell, which is used, can be grown in suspension culture.

To be effective against agents that replicate on the mucosal surfaces a vaccine should induce the local antibodies required for immune protection. Based on this concept, several conventional first generation live rotavirus vaccines are being developed. Formulations for these live vaccines include the use of attenuated human rotavirus strains, animal rotavirus strains or mixed animal-human viruses. The total number of virus groups or virus serotypes that must be included in these live vaccines is undetermined. However, if heterologous viruses are able to produce protective responses in humans and animals the number may be limited.

The present invention discloses an alternate method of vaccine production which avoids the problems associated with live attenuated viruses. This invention discloses the production of rotavirus specific proteins from cloned genes. The present invention discloses a highly efficient production of vaccine from rotavirus genes cloned in baculovirus in infected insect cells. The nonessential structural region of the baculovirus polyhedrin gene viral genome is deleted and the cloned rotavirus gene(s) are inserted into this region such that synthesis is regulated by the viral polyhedrin promoter. One skilled in the art will quickly recognize that engineered cloned genes in bacteria, yeast, mammalian or insect cells using appropriate expression vectors will also produce similar gene products. However, the most efficient appears to be baculoviruses. This efficiency is due in part to the highly active promoter gene at this site.

Thus, the most straightforward and practical approach to developing "second generation vaccines" is to produce rotavirus proteins in a prokaryotic or eukaryotic expression system for direct use as antigens. We have successfully produced proteins from the rotavirus SA11 genes in a baculovirus vector system. The method of the present invention produces synthetic polypeptides which are a very cost effective means of producing a vaccine for immunization in both the developed and the developing world.

We have found that the nature of the baculovirus, as well as the efficient polyhedrin promoter, result in high level expression of the rotavirus major capsid in gene. Furthermore, the baculovirus system overcomes many of the problems associated with high level expression in bacteria. For example, in most bacteria high level production results in a product that is insoluble. Solubilization of these proteins from bacteria requires further purification. Subsequent administration of the proteins as vaccines often results in a significant loss of immunogenicity. In the present system, the strong promoter produces high concentrations of the antigen which is secreted from the cell into the media. The antigen is easily purified since the media composition can be controlled. Therefore, there are minimal problems associated with solubilization and purification. Additionally the easy purification allows for the retention of the native protein state.

Further objects, features and advantages will be apparent from the following description of preferred embodiments of the invention.

DETAILED DESCRIPTION OF THE PREFERRED EMBODIMENTS

Figure 1:
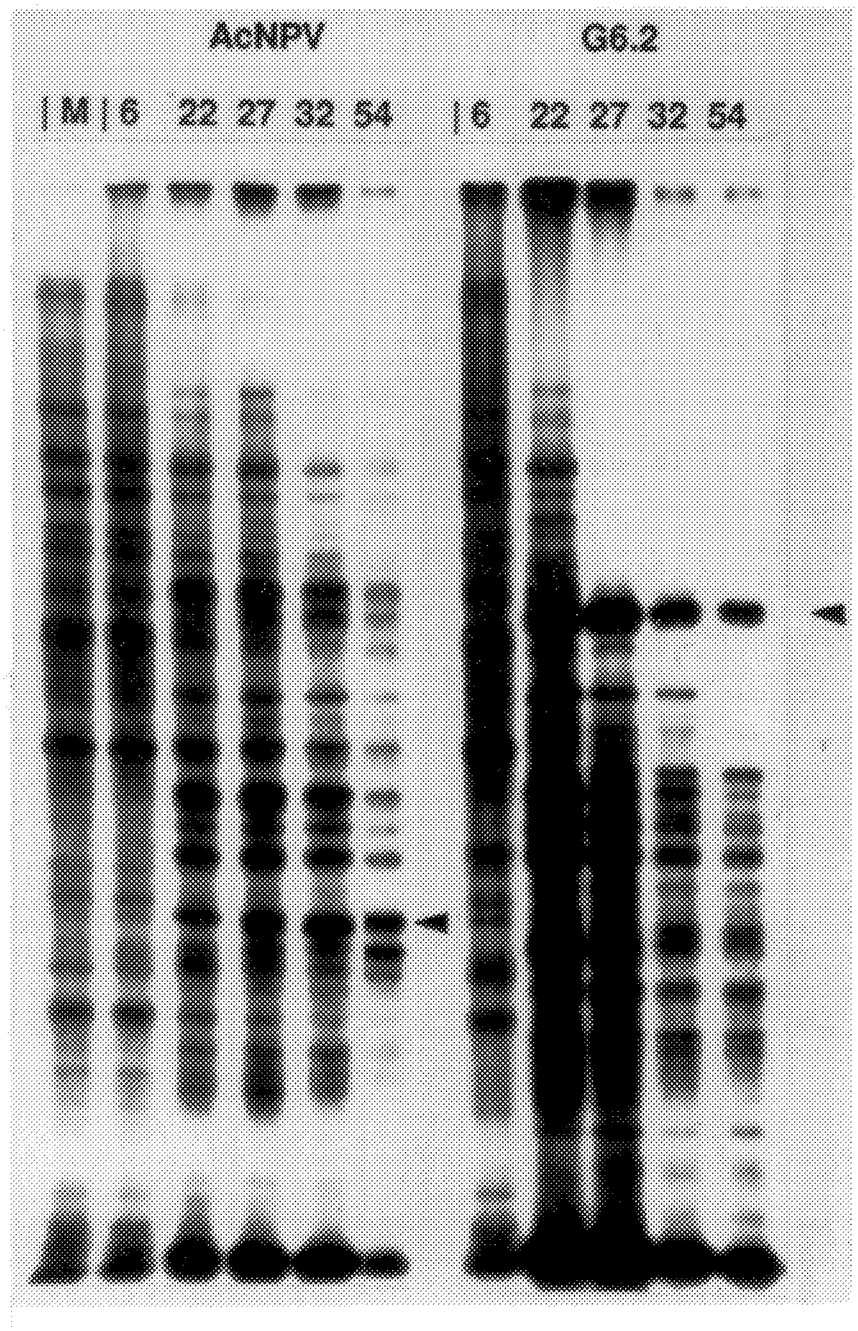
FIG. 1. Kinetics of Protein synthesis of VP6 in infected Sf cells. The proteins synthesized in mock-(M), wild-type baculovirus-(AcNPV) or baculovirus recombinant-infected Sf cells were labeled with $^{35}$S-methionine (30 uCi/ml) at the indicated times (in hours). The proteins in cells harvested 2 hours later were then analyzed in 12% polyacrylamide gels. Polyhedrin and SA11 VP6 are indicated by arrowheads in the left- and right-hand panels, respectively.

The general method for the successful synthesis of foreign proteins from cloned genes in a vector system involves the insertion of the foreign gene downstream from the promoter in the expression vector. Thus the production of the protein from the cloned gene will be controlled through the promoter which directs the transcription of messenger RNA (mRNA).

The procedure involves isolating full length gene clones from rotavirus. These can be isolated from a variety of human or animal virus strains by well known molecular biology techniques. Cloned cDNA is synthesized from genomic double-stranded RNA segments or from mRNA transcribed from these segments by the endogenes viral RNA polymerase. First, strand cDNA is synthesized using reverse transcriptase and double-stranded cDNA is obtained either by hybridization of complementary plus and minus strands synthesized from denatured ds RNA or by second strand sythesis of dC tailed cDNA using reverse transcription or Klenow fragment. Double-stranded cDNA is then tailed with oligo dG and inserted into the Pst-1 site of a bacterial plasmial such as pBR322 or one of its derivatives. After amplification of the cDNA, identification of its gene origin and sequencing to determine it is full-length, the selected gene is subcloned into the baculovirus transfer vector to begin the process to make and select the recombinants. The exact procedures for subcloning each cloned rotavirus gene will vary depending on the gene sequence. In general a restriction endonuclease is used to remove the gene from the original bacterial plasmid. This gene segment is then cloned and inserted into the baculovirus transfer vector. Recombinant transfer vector DNA is then selected by antibiotic resistance to remove any non-recombinant plasmid DNA and subsequently amplified and purified for transfection into *Spodoptera frugiperda* (SF) cells. Standard viral DNA is used to co-transfect *Spodoptera frugiperda* (SF) cells. Putative recombinant viruses containing the recombinant molecules are isolated from the virus yield from these transfected monolayers. Because the polyhedrin structural gene has been removed, plaques containing the recombinant viruses can be easily identified since they lack occlusion bodies. Confirmation that these recombinants contain the desired gene is established by hybridization with specific gene probes.

The expression of rotavirus proteins is determined in SF cells or insects infected with the virus containing the recombinant DNA. The infection process, including viral protein synthesis, viral assembly and partial cell lysis may be complete by approximately 72 hours post-infection. This may be protein dependent and thus may occur much earlier or later. The proteins produced in infected cells are radiolabeled with $^{35}S$-methionine, $^{3}H$-leucine, or $^{3}H$-mannose and both cell-associated and cell-free polypeptides are analyzed by electrophoresis on polyacrylamide gels to determine their molecular weight. The expression of these products is examined at different times post-infection, prior to cell lysis.

Immunological identification of recombinant products is examined by either direct immunoprecipitation or by Western blots. For Western blots, cell-associated proteins or the proteins in the media are separated on SDS polyacrylamide gels, transferred onto nitrocellulose filters, and identified with antiserum to the rotavirus-specific proteins or to the polyhedrin. Specifically bound antibody is detected by incubating the filters with $^{125}I$-labeled protein A or enzyme conjugated anti-antibody, and followed by exposure to X-ray film at −80° with intensifying screens or colorimetic reaction with enzyme substrate.

Alternatively, extracts of cell-associated and soluble proteins are used for immunoprecipitation with monoclonal antibodies or with monospecific or polyclonal antivirus serum, to determine whether rotavirus proteins are being produced. These analyses determine whether the proteins produced in the recombinant-infected insect cells are identical in size with those produced in cell-free translation systems or in rotavirus infected-cells. Finally, the amounts of each protein are quantitated before and following protein purification.

The product(s) produced by the rotavirus gene are similarly analyzed to determine if they are properly processed (i.e., that the signal peptides are cleaved and whether they are correctly glycosylated).

Once recombinant vectors that express the proteins are established, then the cells are infected with different combinations of the recombinants. These viral proteins should form capsid subunits and be released from the infected cells as a subunit. Studies on the morphogenesis and immunologic properties of rotavirus particles will allow the prediction of how viral subunits are assembled in infected cells or in cell-free systems.

The next step is to purify the proteins for use and evaluation as subunit vaccines. In this expression system the rotavirus proteins are often released into the medium. Media from these infected cells is concentrated and the proteins purified using standard methods. Salt precipitation, sucrose gradient centrifugation and chromatography, high or fast pressure liquid chromatography (HPLC or FPLC) is used because these methods allow rapid, quantitative and large scale purification of proteins, and do not denature expressed products. Thus, we achieve the highest probability of producing proteins that retain their antigenic properties.

The efficiency of synthesis of the desired gene product is dependent on multiple factors including: (1) the choice of an expression vector system; (2) the number of gene copies that will be available in the cells as templates for the production of mRNA; (3) the promoter strength; (4) the stability and structure of the mRNA; (5) the efficient binding of ribosomes for the initiation or translation; (6) the properties of the protein product, such as, the stability of the gene product or lethality of the product to the host cells; (7) the ability of the system to synthesize and export the protein from the cells, thus simplifying subsequent analysis, purification and use.

Production of the viral proteins in high yields from expression vector systems provides a novel way to study viral protein function and to develop diagnostic tests and vaccines. This invention discloses and is directed to an evaluation of the antigenic and molecular properties of the simian rotavirus SA11 major capsid protein VP6 and glycoprotein, VP7, as well as the non-structural protein NS28 produced using the baculovirus expression system.

Several properties and advantages of the present invention employing expressed rotavirus proteins will be readily obvious to one skilled in the art. For example, (1) VP6 is not a glycoprotein and is not known to be found in the media from SA11-infected mammalian cells, however, it is present in the media from the baculovirus recombinant-infected cells. Although it is not clear whether VP6 is actively secreted into the media or is released as a result of cell lysis, the property of high concentration in the media greatly facilitates the purification of VP6. Other non-glycosylated proteins, β-galactosidase and chloramphenicol transferase, also are found in the media after production with the same baculovirus expression vector. (2) On the other hand, β-interferon is glycosylated and is also found in the media of recombinant-infected cells. Thus a variety of protein classes can be found in the media, significantly simplifying isolation and purification. (3) Reactivity with available monoclonal antibodies suggested that native immunoreactive determinants were conserved when VP6, VP7 and NS28 were synthesized using the baculovirus expression vector. Additionally, the demonstration that the expressed and purified VP6 protein shows properties of an oligomer, the reported structure of VP6 in virus-infected cells or in virus particles, confirms that the native conformation is maintained in the vector system synthesis. This oligomer formation is associated with disulfide bonds and is an intrinsic property of VP6.

A variety of cultivatable and non-cultivatable strains of rotavirus are known. These strains are known to cause disease in humans and animals. Vaccines against these different strains thus will be useful in combating disease in humans, agricultural animals and pet animals. Examples of these strains in different virus groups are: Simian SA11 and MMU18006; canine CU-1; equine H2 and H1; porcine Gottfried, SB-1, SB-2, OSU, EE and A580; bovine NCDV, UK, B641, B720, B14, II-2 and B223; Turkey Ty1 and Ty3; chicken Ch1; human Wa, KU, K8, DB, DS-1, S2, KUN, HN-126, 390, M, P, YO, 14, 15, McM2, MO, Ito, Nemoto, St. Thomas 4, Hochi, Hosokawa, adult diarrhea rotavirus (ADRV), PaRV and BRVLA. Estes, M. K. et al., "Antigenic Structure of Rotavirus" in Immunochemistry of Viruses. Elsevier p. 389–405 (1985), The disclosure of which is hereby incorporated by reference and; Nakata, S. et al., J. Infectious Diseases 154:448–455 (1986) the disclosure of which is hereby incorporated by reference. Any strain can be used to incorporate the genes into vectors to make recombinant molecules.

SPECIFIC EXAMPLES

MATERIALS AND METHODS

Cells and virus

The simian rotavirus SA11 was grown in cultures of MA104 cells as described in Estes, M. K. et al. J. Virol. 31:810–815, 1979, the disclosure of which is hereby incorporated by reference. The baculovirus *Autographa californica* (AcNPV) and the recombinant virus pAc461/SA11-6 were used to infect *Spodoptera frugiperda* (Sf) (IPLB-SF21-AE) cells at a multiplicity of infection (MOI) of 10 plaque-forming units per cell. Sf cells were grown and maintained on Hink's medium containing 10% fetal bovine serum (FBS) as described in Smith, G. E. et al. J. Virol. 46:584–593, 1983, the disclosure of which is hereby incorporated by reference.

Construction and selection of baculovirus recombinants

Gene 6

SA11 gene 6 was originally in the PstI site of pBR322. The resulting clone, pSA11-6, was digested with AhaIII and HpaII and subcloned into the SmaI site of the baculovirus transfer vector pAc461. The plasmed pAC461 was derived from pAc311 by cleavage with BamHI and kpnI, digestion with Bal31 nuclease, treatment with DNA polymerare I (Klenow fragment) to produce blunt ends, ligation of a SmaI [GCCCGGGG] linker, cleavage with SmaI and religation. The plasmid pAC461 has a deletion between positions −7 and +670 in the baculovirus polyhedrin gene. After transfection into *Escherichia coli,* plasmids in recombinant ampicillin-resistant colonies were screened by restriction enzyme analysis for inserts in the correct transcriptional orientation, and one was designated pAc461/SA11-6. pAc461/SA11-6 is missing the first seven nucleotides of the 5' end of SA11 gene 6 and has about 70 extra base pairs that were added at the 3' end during the original cloning into pBR322. Transfer of SA11 gene 6 cDNA from this vector to the AcNPV genome DNA was achieved by cotransfection of Sf cells with wild-type AcNPV DNA using the calcium phosphate precipitation procedure as described in Smith, G. E., et al. J. Virol 46:584–593, 1983. The AcNPV DNA (1 μg) was mixed with 2 μg of pAc461/SA11-6, and brought to 950 ul with HERBS/CT [0.137M NaCl, 6 mM D-glucose, 5 mM KCl, 0.7 mM $Na_2HPO_4$.7 $H_2O$, 20 mM HEPES, 15 μg/ml sonicated calf thymus (CT) DNA, pH 7.1], and vortexed. While the mixture was being slowly vortexed, 50 ul of 2.5M $CaCl_2$ was added and a precipitate was allowed to form at room temperature for 30 minutes. The precipitated DNA was added to 2 ml of Hink's medium supplemented for 10% FBS in a 25-$cm^2$ flask seeded with $2.5\times10^6$ Sf cells. Following incubation at 27° C. for 4 hours, the medium was removed, the monolayer was washed with fresh Hink's medium containing 10% FBS, and, after the addition of 5 ml of Hink's medium supplemented with 10% FBS, the flask was incubated at 27° C. The cells were observed using an inverted microscope for signs of infection and, at an advanced stage of infection (day 5), extracellular virus was harvested and plaqued on monolayers of Sf cells. Recombinants, in which the polyhedrin gene had been replaced by the polyhedrin-SA11-6 transfer vector DNA by homologous recombination, were selected by identifying occlusion negative plaques with an inverted phase microscope as described in Smith, G. E. et al. J. Virol. 46:584–593, 1983. Virus in occlusion-negative plaques was plaque purified three times and used to propagate virus stocks.

Gene 9

Clones of SA11 gene 9 were constructed using the same procedures as for gene 6 clones (described in Estes, M. K. et al. Nucl. Acid Res. 12:1875–1887, 1984, the disclosure of which is incorporated by reference). These clones were selected from the library of cDNAs using probes for gene 9. The identification of these clones was confirmed by production of the specific protein in cell-free translation systems derived from rabbit reticulocytes and wheat germ extracts. Such translation reactions were programmed with mRNA selected by hybridization to the gene 9 cDNA immobilized on filters. The entire coding sequence of each of these clones was then inserted in the baculovirus transfer vector prior to transfection of Sf cells to obtain baculovirus recombinants containing SA11 gene 9 DNA. For gene 9 constructions, the gene 9 cDNA was excised from pBR322 with Pstl and this DNA was gel purified and inserted into the Pstl site of the pAC461 baculovirus transfer vector. Another alternative is that prior to insertion into pAC461 the tails or other sequences may be modified or deleted. Gene 9 stocks were then obtained following the procedures used for gene 6.

Gene 10

Clones of SA11 gene 10 were constructed using the procedure of Both G. W. et al., J. Virol. 48:335–339 (1983). These clones were selected from the library of cDNAs using probes for gene 10. The identification of these clones was confirmed by production of the specific protein in cell-free translation systems derived from rabbit reticulocytes and wheat germ extracts. Such translation reactions were programmed with mRNA selected by hybridization to the gene 10 cDNA immobilized on filters. The entire coding sequence of each of these clones was then inserted in the baculovirus transfer vector prior to transfection of Sf cells to obtain baculovirus recombinants containing SA11 gene 10 DNA. For gene 10 constructions, the gene 10 cDNA was excised from pBR322 with AHAIII and HpaIII as described for gene 6 and gene 10 was inserted into the SmaI site of the pAC461 baculovirus transfer vector. Gene 10 stocks were then obtained following the procedure used for gene 6.

Radiolabeling analysis of proteins synthesized in infected Sf cells

Sf cells infected with recombinant SA11-6 or recombinant SA11-9 or recombinant SA11-10 or with wild-type AcNPV were radiolabeled at different times post-infection with 15 μCi/ml of $^{35}S$-methionine in methionine-free Hink's medium supplemented with 10% FBS. The cells and media were harvested at 42 hours post-infection, and the cells were pelleted at 1400×g at 4° C. for 5 minutes. The cell-free supernatant was removed and saved for testing, and the cell pellet was suspended in RIPA buffer [0.15M NaCl, 0.01M Tris-HCl (pH 7.2), 1% trasylol, 1% soldium deoxycholate, 1% Triton X-100, 0.1% sodium dodecyl sulfate (SDS)]. Proteins were immunoprecipitated from these samples as described in Chan, W. K. et al. Virology 151:243–252, 1986, the disclosure of which is incorporated by reference. Antisera used for immunoprecipitation were a polyclonal guinea pig anti-SA11 serum (gp αSA11) that reacts with SA11 structural proteins VP 2, 3, 6 and 7; ascites fluids from mice injected with hybridoma cells that secrete monoclonal antibodies to VP6 (gene 6) subgroup I (αSGI) or subgroup II (αSGII) or to a common determinant on VP6 (αcommon); monoclonal or polyclonal antibodies to VP7 (gene 9); or monoclonal antibodies to NS28 (gene 10). In some cases the immunoreactivity of the expressed protein was also analyzed on immunoblots.

Partial purification of the expressed rotavirus Proteins (VP6, VP7 and NS28)

For example, gene 6 recombinant-infected Sf cells were labeled 28 hours post-infection with $^{35}S$-methionine (30 μCi/ml, 1200 Ci/m mole Amersham Corp.) in Hink's medium lacking FBS. The cells and media were harvested separately at different times post-infection by scraping cells into the media and pelleting the cells by centrifugation at 1000 RPM for 20 minutes at 4°. Proteins can be purified from the media or cell-associated material. For example from the media following clarification by centrifugation, 100,000×g for 30 minutes, and then applying the supernatant to a 5 to 20% continuous sucrose gradient for 23 hours at 100,000×g. Fractions containing the expressed proteins that lacked contaminating bovine serum albumin were pooled, dialyzed against 10 mM Tris-HCl (pH 7.5), and used either directly or after lyophilization.

Additionally, wild-type AcNPV and recombinant expressed proteins were prepared by the same infection conditions and harvesting procedure, but not purified further. In this case, medium from infected cells was collected, dialyzed against 10 mM Tris-HCl (pH 7.5), and used directly or lyophilized. Concentrations of proteins were approximated by comparing the amounts of protein to quantitative marker proteins after electrophoresis on 12% polyacrylamide gels and staining with silver nitrate or Coomassie blue or by a quantitative ELISA.

Affinity purification of expressed proteins

Protein A-Sepharose CL-4B affinity columns (Pharmacia Inc.) were prepared by crosslinking monoclonal antibody supernatant to the gel using dimethylpimelimade dihydrochloride. Unlinked antibody was removed by washing with 0.1M borate buffer (pH 8.3). Supernatants from Sf cells infected with the appropriate recombinant genes were mixed with the immunomatrix, shaken at room temperature, and centrifuged at 1500 RPM for 1 minute. The immunomatrix gel was then suspended in borate buffer and poured into a disposable Econocolumn (Bio Rad). The column was washed sequentially with 50 ml each of buffer A [0.5M NaCl, 0.05M Tris-HCl (pH 8.2), 1 mM EDTA, 0.5% Nonidet P-40], buffer B [(0.15M NaCl, 0.05M Tris-HCl (pH 8.2), 0.5% Nonidet P-40, 0.1% SDS], and buffer C (0.15M NaCl, 0.5% sodium deoxycholate) with borate buffer washes between each. After a final wash with borate buffer, the protein was eluted from the gel with 0.1M glycine-HCl (pH 2.5) into tubes containing 2M Tris base to neutralize the acid. The eluted protein was analyzed by electrophoresis on 12% polyacrylamide gels and was used as a standard in ELISA to quantitate the kinetics and levels of expression of the proteins VP6, VP7 or NS28. For example and not limitation subgroup I (βSGI) monoclonal antibody can be used to purify VP6. One skilled in the art will readily recognize that specific monoclonal antibodies to other rotavirus proteins can be used to purify these proteins.

Production of antiserum to expressed proteins

Guinea pigs (Elm Hill Breeding Farms, Chelmsford, Mass.) shown to lack rotavirus antibodies were used for the production of antiserum to expressed VP6 protein. Each guinea pig was inoculated intramuscularly twice at 3-week intervals as described in Estes, M. K. et al. J. Virol. 31:810–815, 1979. The antigens used were partially purified expressed VP6, or proteins concentrated from the supernatant from Sf cells infected with either AcNPV or pAc461/SA11-6. The guinea pigs were bled 1 week after the second injection of antigen, and the serum samples were tested for the presence of antibodies by immunofluorescence, immunoprecipitation, ELISA and immune electron microscopy assays. VP6 is shown for example and similar methods are used to produce antiserum to to other rotavirus proteins including VP7 and NS28.

SDS-Polyacrylamide gel electrophoresis

Protein products were analyzed by polyacrylamide slab gel electrophoresis using a modification of the method of Laemmli with 12% separating and 4% stacking gels as described in Chan, W. K. et al. Virology 151:243–252, 1986. Before electrophoresis, unless otherwise stated, samples were dissociated by boiling for 3 minutes in sample buffer containing 1% SDS, 10% 2-mercaptoethanol, 0.5M urea, 0.05M Tris HCl (pH 6.8), 10% glycerol, and 0.0025% phenol red. Radiolabeled proteins were monitored on gels following fluorography, as described in Mason, B. B. et al. J. Virol. 46:413–423, 1983, the disclosure of which is incorporated by reference.

Expression of SA11 Proteins in Sf cells

Three baculovirus recombinants containing an SA11 gene 6 cDNA insert were initially identified and tested for their ability to produce SA11 VP6 after infection of Sf cells. The $^{35}$S-methionine containing polypeptides in cells infected with AcNPV or SA11 gene 6 recombinant are shown in FIG. 1. A new band at the expected molecular weight of 41,000 (41K) was seen in recombinant-infected cells while the polyhedrin protein was only seen in AcNPV-infected cells. The kinetics of synthesis of this protein demonstrated that the radiolabeled VP6 is initially detected at 22 hours post-infection, and its synthesis is still detectable at 105 hours post-infection. One skilled in the art will recognize the advantages of this late synthesis for identification and isolation of foreign protein (rotavirus) from early synthesized protein (baculovirus). Protein VP6 is shown for example only and not limitation. Other gene products of rotavirus can be similarly expressed and detected in Sf cells.

Immunoreactivity and localization of expressed proteins

Figure 2:
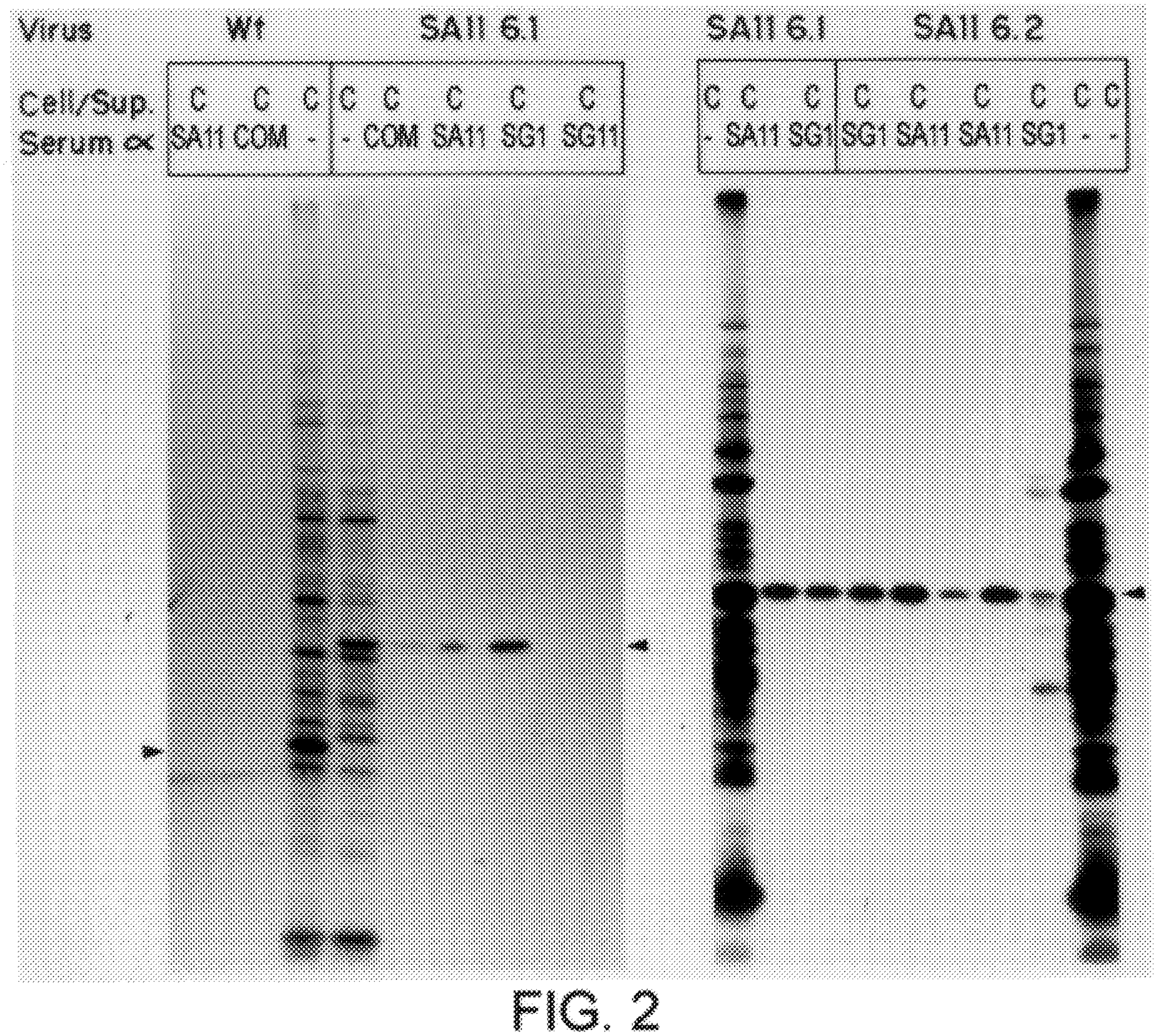
FIG. 2. Expression and immunoreactivity of SA11 VP6 in Sf cells. $^{35}$S-methionine-labeled proteins synthesized in Wt or SA11 gene 6 recombinant infected Sf cells. AcNPV polyhedrin (►—) and SA11 VP6 (—◄) are highlighted. The immunoreactivity of these proteins with antiserum to SA11 particles (αSA11) or with monoclonal antibodies to epitopes present (αSGI, αcom) or absent (αSGI) on SA11 VP6 is shown. The left-hand panel shows reactivity of cell-associated VP6 while the panel on the right shows reactivity with VP6 from cells (C) or from the media supernatant (S) from cells infected with two different gene 6 recombinants.

Identification of the 41K band as authentic VP6 was shown by positive immunoreactivity with polyclonal antisera prepared to SA11 virus and with monoclonal antibodies to two epitopes (common and subgroup I) on the SA11 VP6 (FIG. 2). Specificity of these reactions was shown by a lack of reactivity of the subgroup II antibody with the SA11 41K protein and by finding that no proteins in AcNPV-infected cells reacted with any of these areas. Similar results were found with all three VP6 recombinants.

Figure 3:
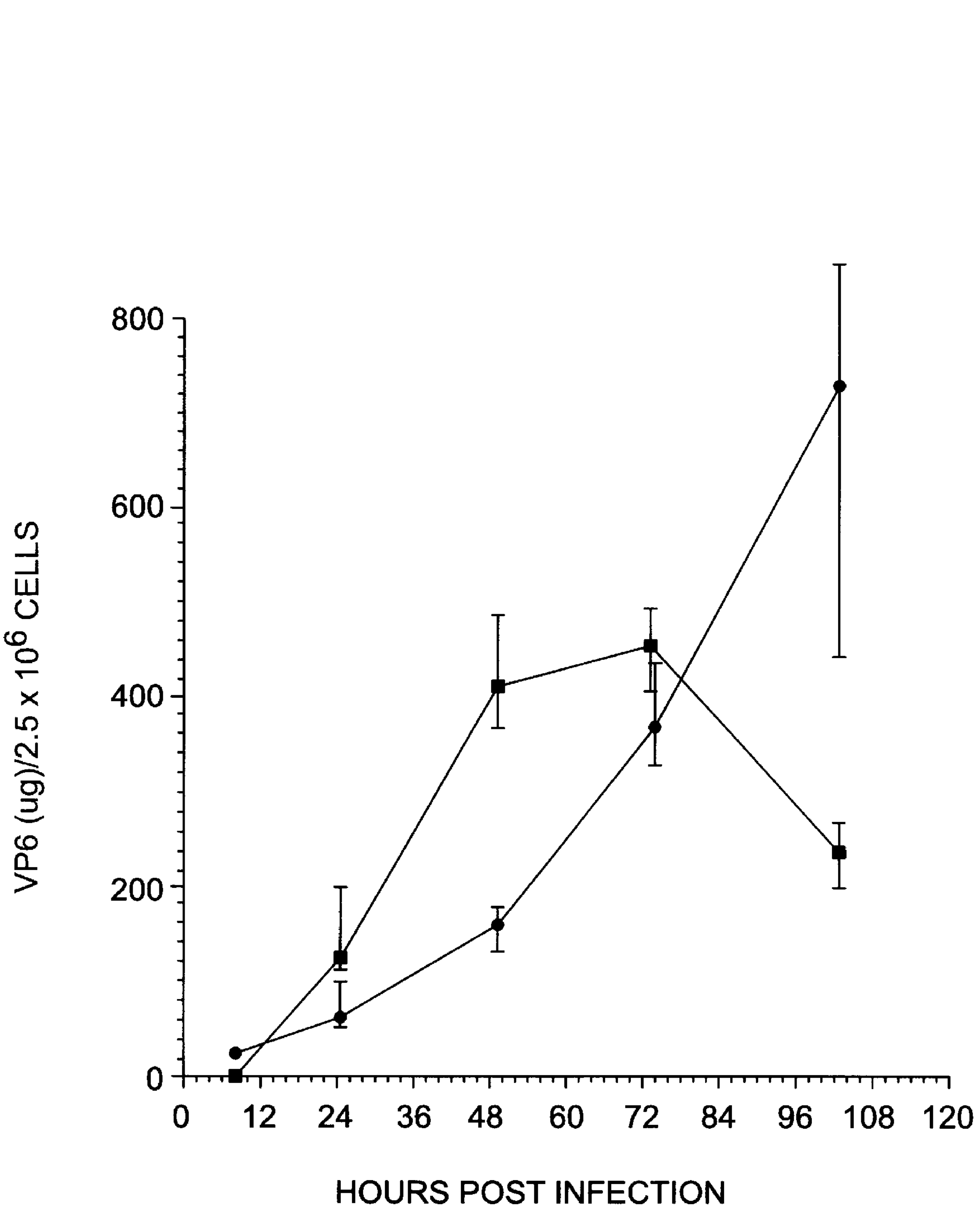
FIG. 3. Detection of VP6 expression by ELISA. ELISA results showing amounts of VP6 detected by ELISA in media (●) or in SA11-infected Sf cells (■) at the indicated times postinfection. The amounts of VP6 at each time-point were quantitated by direct comparison of the optical density (OD) readings of SA116.1-infected cell samples with the OD values on a standard curve of a known amount of affinity-purified VP6. Background OD values (0.001–0.016) from mock and wt AcNPV-infected cells were subtracted. The range of the amounts of VP6 detected in different infections are also shown.

VP6 was observed in the cytoplasm of recombinant-infected cells by immunofluorescence, and it could be immunoprecipitated from both clarified supernatants and cell-associated proteins (FIG. 2). The amount of protein being synthesized can be quantitated by analysis of dilutions of immunoprecipitated VP6. FIG. 3 shows quantitation with ELISA standardized with VP6 purified to radiochemical and biochemical homogeneity from an immunomatrix column and demonstrates that immunoreactive VP6 could be detected as early as 8 hours post-infection. Furthermore the amount of VP6 found in the medium increased with time. The cell-associated VP6 was produced in infected cells in amounts of 20–150 $\mu$g from a density of $10^6$ cells/ml, and these yields in clarified media are sufficient for further biochemical and immunologic studies using purified VP6. The yield of VP6 is maximized when cells were grown in complete media containing 10% FBS.

Conformational properties of expressed VP6

Figure 4:
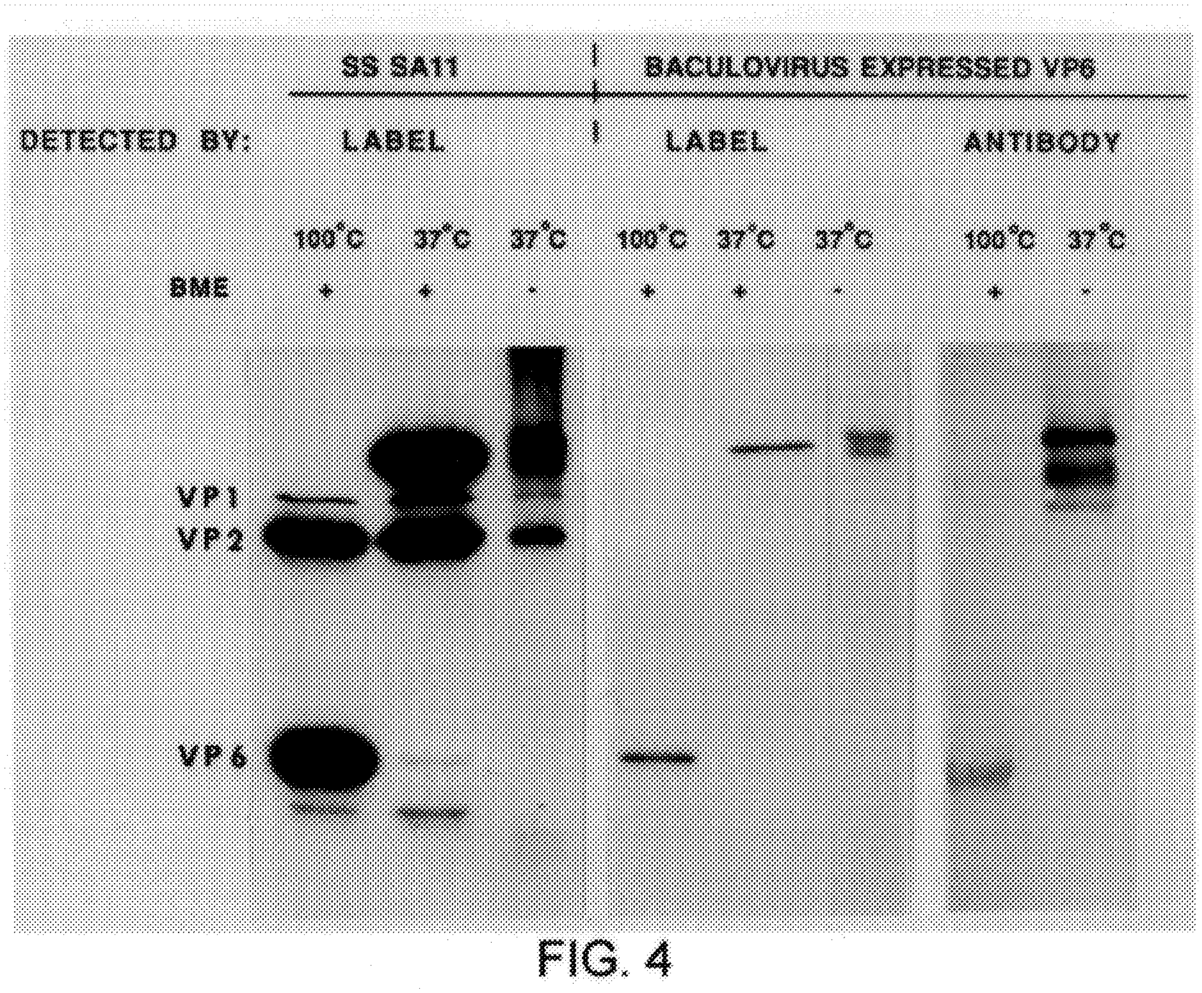
FIG. 4. Comparison of conformation of expressed and authentic VP6. The polypeptide(s) in single-shelled (ss) SA11 particles or in baculovirus-expressed VP6 were separated on 12% polyacrylamide gels after heating either at 100° C. for 2 minutes or at 37° C. for 30 minutes in sample buffer in the presence (+) or absence (−) of 2-mercaptoethanol (BME). The gels were processed for fluorography and exposed to film to detect radiolabeled proteins or the separated proteins were electrophoretically transferred to nitrocellulose and then detected using the SGI monoclonal antibody.
Figure 6A:
FIG. 6. Assembly of expressed VP6 into structures with capsomere-like morphology. Expressed VP6 was partially purified and its structure was examined by electron microscopy following staining with 2% aqueous uranyl acetate. Tubular structures that were assembled in vitro were observed. These structures show hexagonal subunit arrangements typical of the rotavirus inner capsid. Confirmation that these subunits contain VP6 was shown by specific immunologic reactivity with anti-SGI serum but not with anti-NS28 serum. The antisera had been conjugated to colloidal gold to facilitate visualization of antibody reactivity.
Figure 6B:
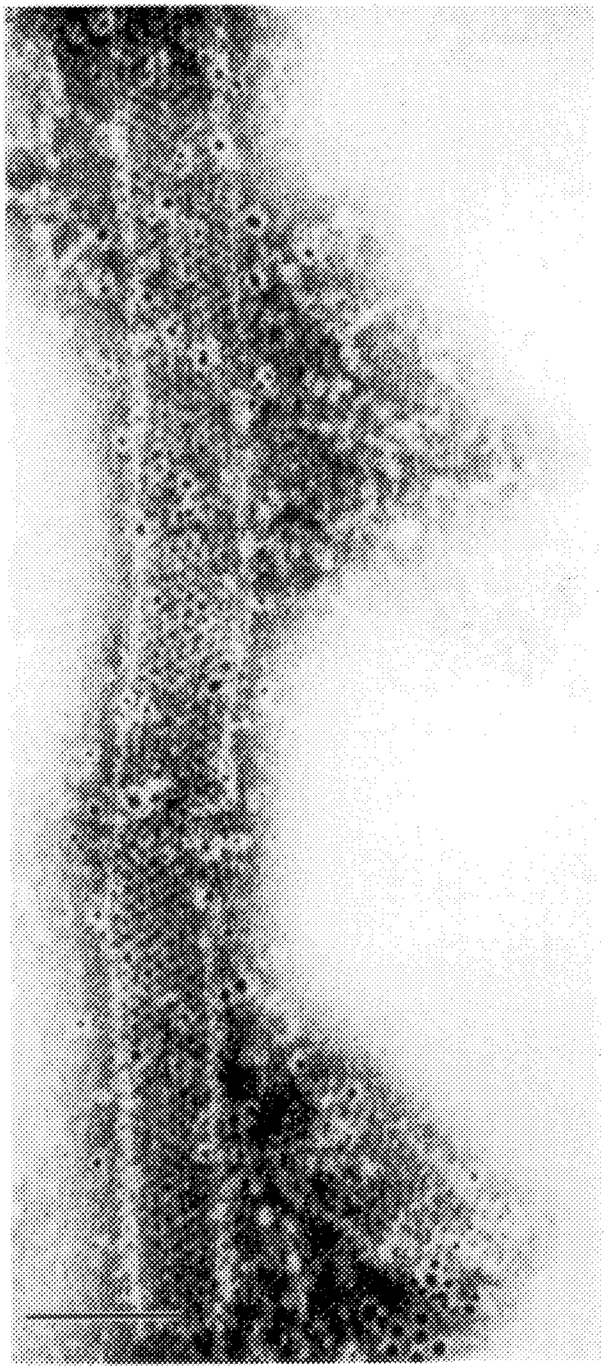
Figure 6C:
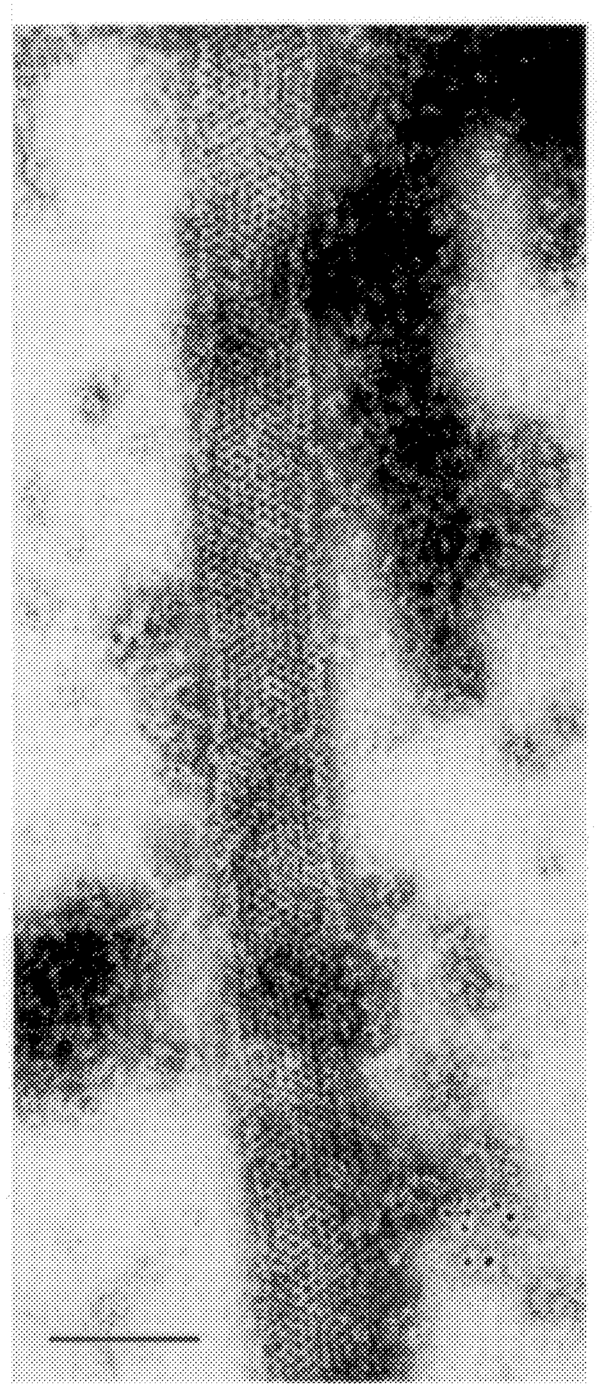

It is known that VP6 removed from purified bovine rotaviruses or analyzed in infected cells behaves as an oligomeric, possibly trimeric, protein. The VP6 synthesized in the present invention possessed conformational properties similar to authentic VP6. VP6 purified from the media form infected cells possessed a native oligomeric structure, was immunogenic in guinea pigs, and was able to spontaneously assemble into morphologic subunits. FIG. 4 shows that the profile of $^{35}$S-methionine-labeled proteins in purified single-shelled virus after electrophoresis in SDS-polyacrylamide gels was different depending on whether or not the virus was heated prior to loading the gels. In the presence of heating, characteristic bands representing VP1 (125K), VP2 (94K), and VP6 (41K) were seen. In the absence of heating, the VP6 band disappeared and a new band migrating above VP1 was observed. Similar analyses with baculovirus-expressed VP6 (partially purified on sucrose gradients) and with immunoaffinity-purified VP6 showed that these proteins also formed oligomers (FIG. 4). In the absence of reducing agents (2-mercaptoethanol), an additional band that also migrated as a multiple oligomeric form was observed. Monomeric and oligomeric forms of expressed VP6 were also seen using immunoblots. One skilled in the art will recognize that the immunoprecipitation studies with monoclonal antibodies and the conformational studies confirm that the expressed VP6 possesses a native conformation and furthermore demonstrates that oligomer formation is an intrinsic property of VP6. FIG. 6 shows electron micrographs of the expressed VP6 that assembled spontaneously into morphological structures. These tubular structures that are expressed VP6 show hexagonal subunit arrangements typical of the rotavirus inner capsid. FIG. 6B shows the VP6 structures labeled with SGI-gold complex. FIG. 6C shows the VP6 structure reacted with α-NS28-gold complex and no specific binding is observed. This shows the specificity of the tubular structures assembled from VP6.

Characterization of antisera produced to expressed protein

Figure 5:
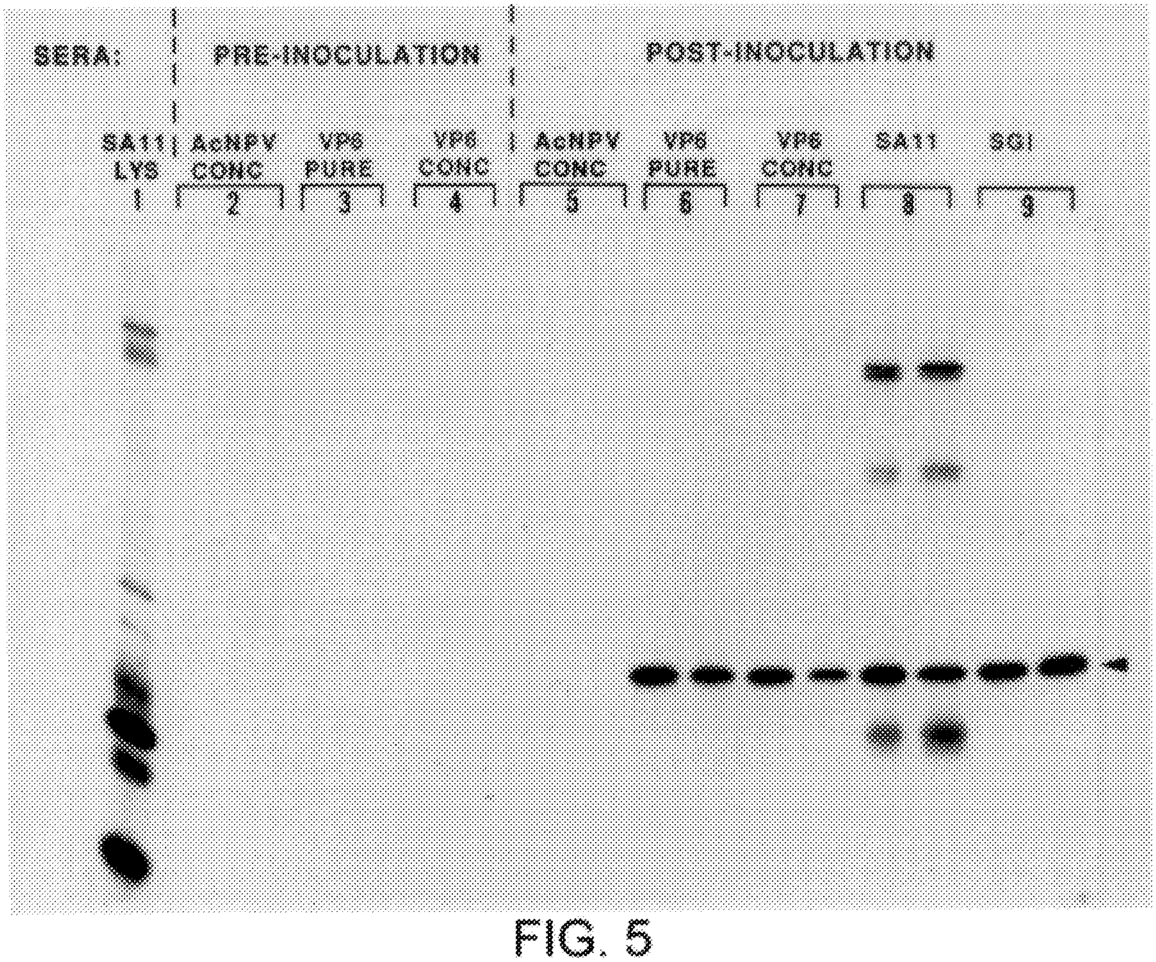
FIG. 5. Characterization of guinea pig antiserum produced to expressed VP6. $^{35}S$-methionine-labeled polypeptides in SA11-infected MA104 cells (lane 1) were immunoprecipitated with guinea pig antiserum made to concentrated proteins from wild-type baculovirus (AcNPV) -infected Sf cells (lane 5); VP6 purified from recombinant-infected Sf cells (lane 6); concentrated (but unpurified) proteins from SA11-6-infected Sf cells (lane 7); or purified double-shelled SA11 (lane 8). Lane 9 shows VP6 immunoprecipitated with monoclonal antibody to the SGI epitope on VP6. Pre-immune serum from all animals showed no reactivity with any proteins from these lysates (lanes 2–4). Viral proteins VP2, VP3, VP5, VP6 and VP7 that react with antiserum to double-shelled virus are seen in lane 8; VP6 is highlighted with an arrow. Lanes 2–9 show analyses performed using undiluted or a 1:10 dilution of the indicated serum.

Antisera were produced in guinea pigs to concentrated wild-type AcNPV-infected Sf cell proteins, to concentrated gene 6 recombinant-expressed proteins in Sf cells, and to VP6 partially purified from the media of infected Sf cells by sucrose gradient centrifugation. The ability of each antiserum to recognize VP6 was tested by immunoprecipitation. In FIG. 5 it can be seen that each pre-immune serum and the antiserum to the AcNPV-infected Sf proteins did not react with any cellular or viral proteins in the SA11-infected MA104 cell lysates, while antisera to the unpurified and to the partially purified VP6 reacted specifically with VP6. These antisera were further characterized for their ability to detect rotavirus. The anti-VP6 sera detected rotavirus strains representing each known human serotype and subgroup with both immunofluorescence and ELISA assays.

Vaccination with baculovirus expressed protein

Mouse dams were vaccinated with parenteral immunization with VP6. The regimen included three doses, each containing 20 $\mu$g VP6 and an adjuvant. As controls, dams were immunized with double-shelled virus, single-shelled virus or adjuvant alone. All pups born to these dams were challenged with rotavirus. Pups whose dam was immunized with double shelled-virus were totally protected from illness. Pups showed partial protection if their dams had been immunized with VP6 or single-shelled virus. These pups experienced both a delayed onset of illness and less severe disease. Pups born to dams only immunized with adjuvant showed rapid onset and severe disease. One skilled in the art will recognize the immunization qualities of VP6. Its pattern suggests that complete protection may require both inner and outer coat antigens. Thus one skilled in the art will further recognize that mixtures of VP6 and VP7 should provide adequate immunization. As other rotavirus proteins are synthesized, additional mixtures can be formed to provide complete immunization against rotavirus infection. One skilled in the art will recognize that several approaches can be used to form mixtures.

For example, these can include the simultaneous infection of Sf cells with more than one recombinant, whereby the intrinsic properties of VP6 and VP7 can foster the formation of aggregates naturally. Experiments with the proteins in Sf cells co-infected with VP6 and VP7 suggest oligomers of these proteins are formed. Since VP6 expressed alone is made as an oligomer and forms morphologic subunits in vitro one skilled in the art will recognize that the co-expressed VP6 and VP7 will naturally form aggregates or subviral particles. Since VP7 is reported to be the cell attachment protein, the expression of these epitopes on the aggregates may enhance the ability of the subunit vaccines to bind to cells and to be a potent immunogen. The co-expression of various combinations of rotavirus gene proteins for example VP6, VP7 VP3, NS28 and others in Sf should result in natural aggregates and thus the production of mixed antigens for immunization in human populations.

Alternatively the rotavirus proteins can be synthesized individually in Sf cells and then a vaccine may be formed by mixing the purified proteins in vitro. Additionally the immungenicity can be improved over straight mixtures by solubilization before or during mixing. Solubilization of the proteins allows in vitro aggregation of the mixed antigens. The aggregates should be better immunogenes than simple mixtures of purified proteins since they simulate the natural state.

Since other modes of mixing including co-synthesis and co-expression can be equally utilized to achieve a mixed antigen immunization vaccine, the above are for example only.

VP6 was immunogenic in that it induced antisera in guinea pigs that was high titer when tested by ELISA or immunofluorescence assay. However, the anti-VP6 sera by itself did not neutralize SA11 infectivity when tested in plaque-reduction neutralization assays using 50 plaque-forming units of virus. Thus there is evidence that even though some in vitro tests do not recognize the immunogenicity of the VP6 protein, actual immunization in vivo can be achieved (mouse data). The inability of the expressed VP6 to induce neutralizing antibodies does not rule out a possible role for this protein in inducing protection from infection or disease, as our understanding of the immunologic and non-immunologic mechanisms that are critical to induce protection from rotavirus infection and disease remains incomplete. VP6 may be important in stimulating cell-mediated immune responses that induce reported heterotypic immunity in a similar fashion to that of the proteins of influenza virus. Expressed VP6 may also be a useful component in subunit vaccines containing additional expressed outer capsid proteins.

Production of Diagnostic Kits for Rotavirus Detection

Antiserums produced to the baculovirus expressed proteins can be used to produce diagnostic kits to detect either rotavirus antigen or antibody responses to rotaviruses. One skilled in the art will recognize that a variety of different formats can be used to produce these diagnostic kits. For antigen detection, antiserum made to one or more of the baculovirus expressed rotavirus proteins is used to detect virus particles or soluble antigen found in clinical specimens. Fecal specimens are preferred since the infection is in the gastrointestinal tract. Antiserum made to VP6 is broadly reactive and detects human and animal rotaviruses. Such kits can also use more than one antiserum made to whole virus particles or to other baculovirus expressed proteins to capture viral antigens. For antibody detection, the antiserum made to the baculovirus expressed protein can be used to capture viral antigen which is then used to detect antibody in human or animal serum samples.

Individually expressed VP6 formed oligomers, and electron microscopic analysis also revealed further assembly of the expressed trimeric VP6 molecules into morphologic subunits that are characteristic of those found on single-capsid particles. These subunits have been seen following selective removal of VP6 from the inner capsid of virus particles. Therefore, protein-protein interactions with other viral proteins or with preformed subviral structures may not be required for subunit formation. The availability of large amounts of purified capsid proteins will now facilitate dissection of the factors that control particle morphogenesis and will allow self-assembly of virus capsids. The native conformation of the present invention is consistent with the use and advantages of this system to produce eukaryotic proteins.

One skilled in the art will recognize other uses of this expressed protein to improve current diagnostic tests for rotaviruses or as a vaccine. Antiserum made to unpurified or partially purified VP6 detected common antigenic determinants shared by all group A rotaviruses by immunofluorescence and ELISA tests. Since VP6 is the major protein detected in available commercial diagnostic tests based on either monoclonal or polyclonal antiserum, it is readily apparent to one skilled in the art that future production of such reagents using baculovirus-expressed VP6 becomes cost-effective due to the high yields and the ability to produce this protein from infected cells grown in spinner cultures, monolayer or fermentation.

While presently preferred embodiments and examples of the invention have been given for the purposes of disclosure, changes therein and other uses will occur to those skilled in the art which are encompassed within the spirit of the invention or defined by the scope of the appended claims.

What is claimed is:

1. A recombinant molecule, comprising:

(a) a baculovirus gene promoter;

(b) a rotavirus gene which codes for rotavirus protein VP7, said promoter spatially positioned in relation to said gene effective to regulate the expression of said gene.

2. A recombinant molecule according to claim 1, wherein said baculovirus gene promoter is a polyhedrin gene promoter from a baculovirus *Autographa californica* nuclear polyhedrosis virus.

3. A method of producing a recombinant molecule comprising the steps of:

(a) inserting a rotavirus gene, coding for rotavirus protein VP7, into a baculovirus transfer vector;

(b) transferring said rotavirus gene in the baculovirus transfer vector to the baculovirus *Autographa californica* nuclear polyhedrosis virus genome DNA by cotransfection of *Spodoptera frugiperda* with wild type *Autographa californica* nuclear polyhedrosis virus DNA;

(c) selecting the recombinant polyhedrin promoter-rotavirus gene molecule by identifying occlusion-negative plaques, or by hybridization with specific gene probes or by both procedures;

(d) purifying said plaques to obtain virus stocks containing recombinant molecule.

* * * * *